Figure 1:
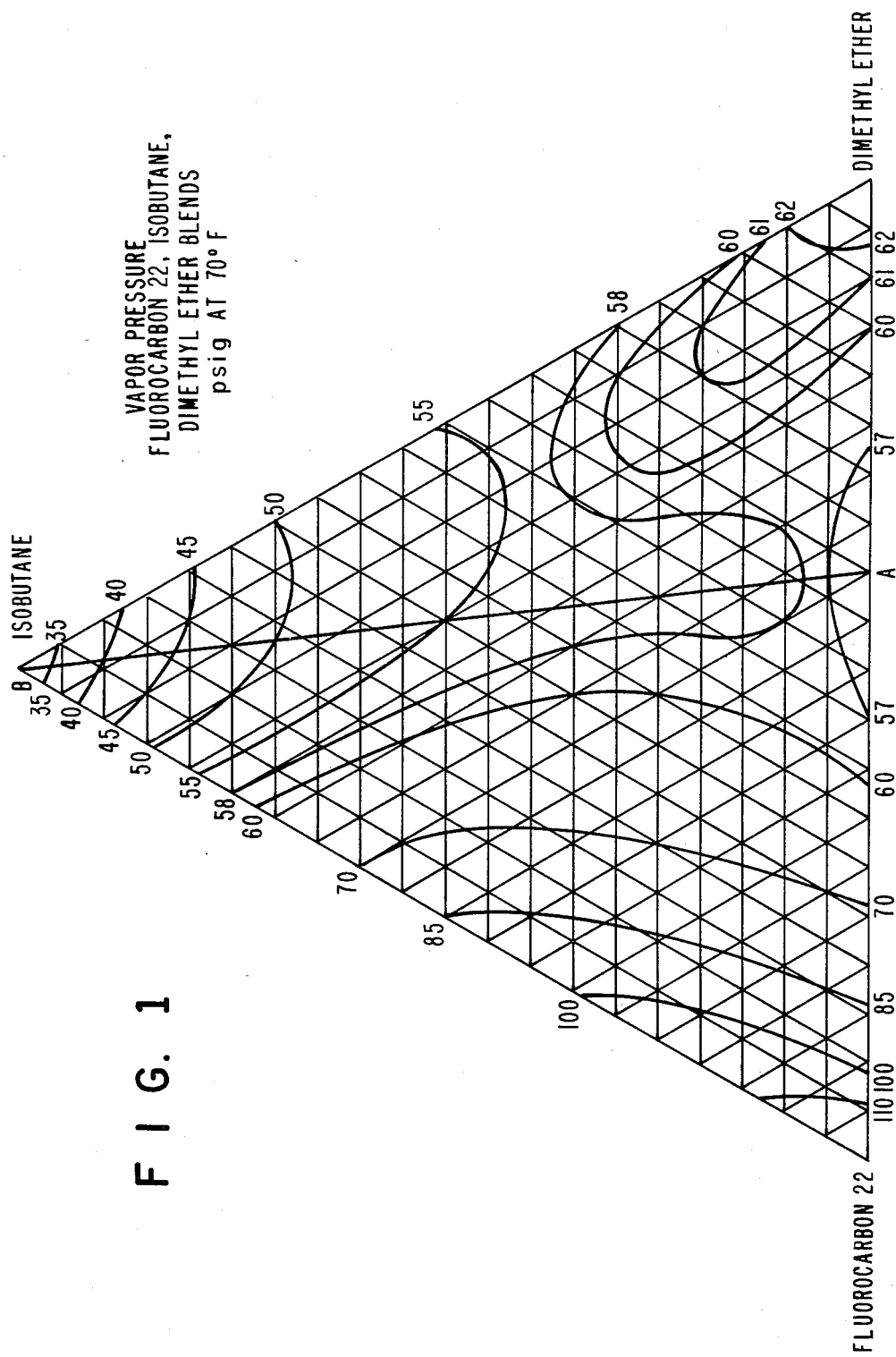

United States Patent [19]

Bartlett et al.

[11] Patent Number: 4,595,522

[45] Date of Patent: Jun. 17, 1986

[54] AEROSOL PROPELLANTS OF MONOCHLORODIFLUOROMETHANE, DIMETHYLETHER AND BUTANE

[75] Inventors: Philip L. Bartlett; John J. Daly, Jr.; John D. Sterling, Jr., all of Wilmington, Del.

[73] Assignee: E. I. Du Pont de Nemours and Company, Wilmington, Del.

[21] Appl. No.: 560,727

[22] Filed: Dec. 12, 1983

[51] Int. Cl.$^4$ .................. C09K 3/30; C11D 17/00; A61L 9/04; A61K 7/00

[52] U.S. Cl. ..................... 252/305; 252/90; 424/45; 424/47; 424/76

[58] Field of Search ............ 252/305, 90, 10; 424/45, 47, 76, DIG. 1

[56] References Cited

U.S. PATENT DOCUMENTS

| | | | |
|---|---|---|---|
| 2,524,490 | 10/1950 | Boe | 252/305 |
| 2,959,325 | 11/1960 | Beard | 221/1 |
| 3,590,006 | 6/1971 | Page et al. | 252/305 X |
| 3,697,434 | 10/1972 | Shefler | 252/188.3 |
| 3,839,220 | 10/1974 | Barchas | 252/305 |
| 3,910,848 | 10/1975 | Froehlich et al. | 252/90 |
| 3,922,228 | 11/1975 | Hutchinson | 252/305 X |
| 4,062,795 | 12/1977 | Hutchinson | 252/305 X |
| 4,145,411 | 3/1979 | Mende | 424/45 |
| 4,152,416 | 5/1979 | Spitzer et al. | 424/45 X |
| 4,174,295 | 11/1979 | Bargigia et al. | 424/47 X |
| 4,198,313 | 4/1980 | Bargigia et al. | 424/45 X |
| 4,382,078 | 5/1983 | Berkhoff et al. | 424/45 |
| 4,444,745 | 4/1984 | Jacobson | 424/45 |

OTHER PUBLICATIONS

Derwent Abstract of Japanese Patent No. 530 866 88, Jan. 1977.

Derwent Abstract of German Patent No. 2,042,267, Aug. 1970.

Derwent Abstract of Netherlands Patent No. 7,107,668, Jun. 1971.

Primary Examiner—Edward A. Miller
Assistant Examiner—Catherine S. Kilby

[57] ABSTRACT

Propellant gas compositions for aerosol products are disclosed consisting essentially of monochlorodifluoromethane, dimethyl ether and a hydrocarbon selected from the group consisting of butane, isobutane and mixtures thereof, said compositions having a vapor pressure of about 50 to 60 psig at 70° F.

9 Claims, 2 Drawing Figures

AEROSOL PROPELLANTS OF MONOCHLORODIFLUOROMETHANE, DIMETHYLETHER AND BUTANE

BACKGROUND OF THE INVENTION

1. Field of the Invention

This invention relates to propelling gas systems for aerosol products.

2. Description of the Prior Art

Many products designed for household, personal or industrial use are available as aerosol products. Typical examples of such products and ones in which the propellant system of the present invention can be used include personal products such as hair sprays, deodorants and colognes; household products such as waxes, polishes, pan sprays, room fresheners and household insecticides; industrial products such as cleaners, lubricants, and mold release agents; and automotive products such as cleaners and polishes. All such products utilize the pressure of a propellant gas or a mixture of propellant gases (i.e., a propellant gas system) to expel the active ingredients from the container. For this purpose, most aerosols employ liquified gases which vaporize and provide the pressure to propel the active ingredients when the valve on the aerosol container is pressed open.

An important physical property associated with the dispensing of aerosol products is the vapor pressure of the propellant. Vapor pressure from the viewpoint of this invention is the pressure exerted when a liquified propellant gas is in equilibrium with its vapor in a closed container, such as an aerosol can. Vapor pressure can be measured by connecting a pressure gauge to the valve on an aerosol can or gas cylinder containing the vapor/liquid mixture. A standard of measurement of vapor pressure in the U.S. aerosol industry is pounds per square inch gauge (psig) with the gas/liquid mixture at constant temperature, most commonly at 70° F. When vapor pressure is mentioned in the ensuing specification without reference to temperature, it can be assumed that the pressure is determined at 70° F. The vapor pressures of liquified gases most widely employed as aerosol propellants will vary over the range of about 20 to 90 psig at 70° F. However, for a great many aerosol products, propellants with a vapor pressure in the range of about 50 to 60 psig are most desirable. The propellant systems of the present invention have vapor pressures in this latter range.

SUMMARY OF THE INVENTION

The present invention pertains to aerosol propellant compositions containing the azeotrope of monochlorodifluoromethane and dimethyl ether (DME). This azeotrope which consists of 40% by weight of monochlorodifluoromethane (more commonly referred to in the industry as fluorocarbon 22 of FC-22) and 60% by weight of dimethyl ether is a maximum boiling ($-9°$ F.) minimum vapor pressure (55 psig at 70° F.) azeotrope. It has been found that this azeotrope in admixture with butane or isobutane or mixtures thereof produces useful aerosol propellants with a vapor pressure in the range of about 50 to 60 psig over a wide range of proportions with respect to the amount of the hydrocarbon present. In the case of isobutane, this hydrocarbon can be used in admixture with the FC-22/DME azeotrope in amounts of about 1-70% by weight based on the total propellant composition, and the vapor pressure of the gas mixture is still within the desired range of about 50 to 60 psig. A preferred range for isobutane content is 50-70% by weight of the propellant gas composition. In the case of butane, the amount of this hydrocarbon can range from about 1 to 39% by weight based on the total propellant composition, and with this construction, a vapor pressure of about 50 to 60 psig is achieved.

It is also possible to use mixtures of butane and isobutane with the FC-22/DME azeotrope to produce the propellant systems of this invention. The proportion of butane to isobutane is not particularly critical. Generally, mixtures of the FC-22/DME azeotrope with 1-40% by weight based on total propellant composition of a blend of butane and isobutane will produce propellant systems with vapor pressures in the range of about 50 to 60 psig.

Figure 2:
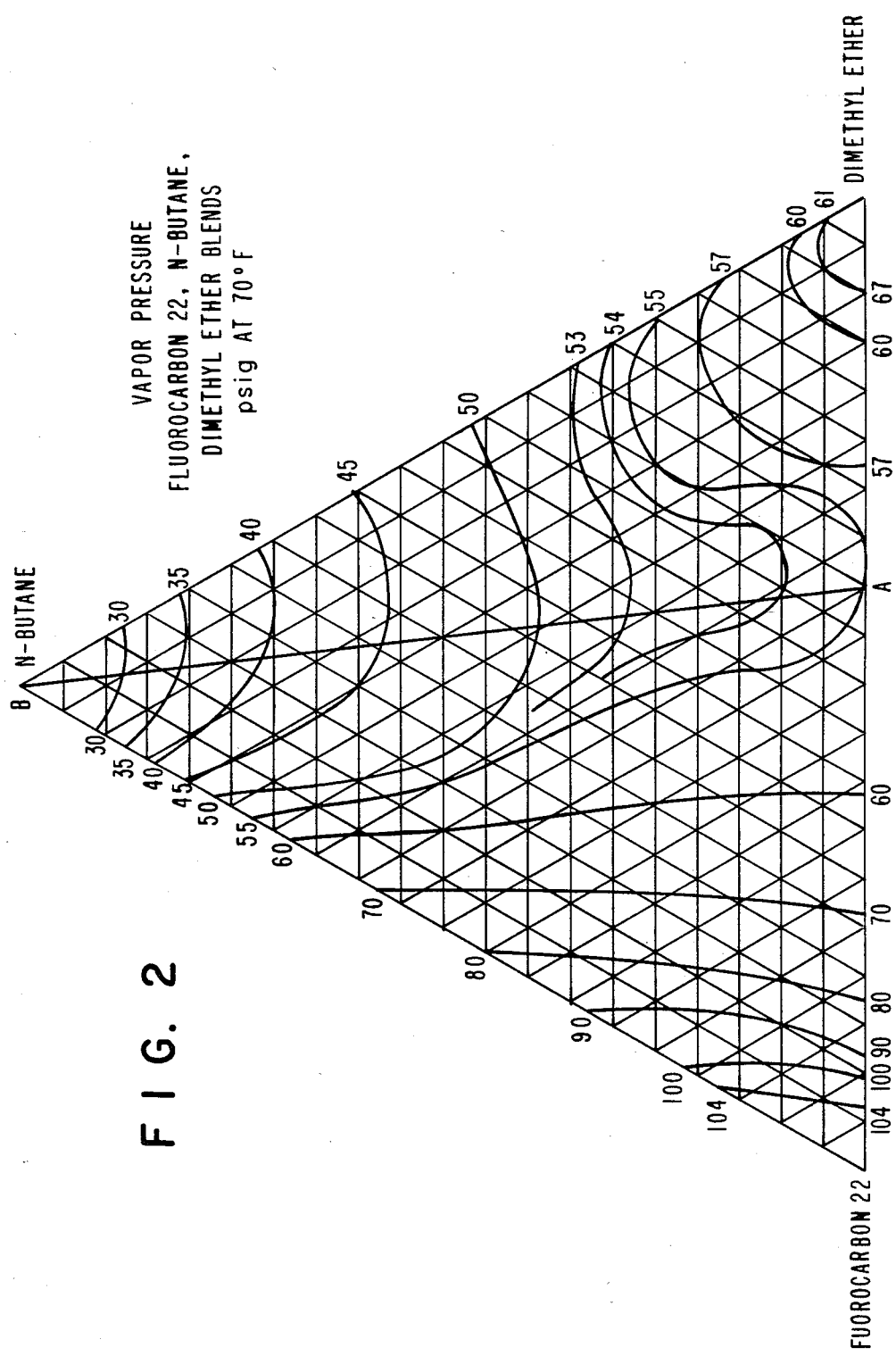

Referring to the drawings, FIGS. 1 and 2 are triangular coordinate charts of the type commonly used in the aerosol industry to illustrate the relationship of concentration and vapor pressure for 3-component systems.

FIG. 1 pertains to the 3-component system consisting of FC-22, dimethyl ether and isobutane.

FIG. 2 pertains to FC-22, dimethyl ether and butane.

In the charts as shown, a concentration of 100% by weight of a particular component is at the vertex of the triangle where the name of the component appears. A concentration of zero percent of this same component is on the side of the triangle opposite this vertex. A composition representing $33\frac{1}{3}\%$ by weight of each component is at the center of the triangle. The parallel lines leading away from each vertex are spaced at 5 weight percent intervals. The curved lines within the triangle with the same number appearing at each end of the line indicate the makeup of formulations of the three components that exert a vapor pressure designated by the number at the end of the line. These lines are the result of measuring the vapor pressure of a large number of specific compositions until sufficient data points are obtained to accurately draw each vapor pressure line. Each of these vapor pressure lines represents one particular pressure. There is also shown on the charts a line AB extending from the base of the triangle at the point representing the composition of the FC-22/DME (40/60) azeotrope to the apex of the triangle at point B which represents 100% hydrocarbon. Determination of the vapor pressure of any given composition comprising the azeotrope and isobutane can be quickly ascertained by locating the point on this line in FIG. 1 that corresponds to the isobutane content of the mixture. The vapor pressure line in closest proximity to this point enables one to closely estimate the vapor pressure of the given composition. Further, it will be apparent from looking at the vapor pressure lines that cross line AB in FIG. 1, that about 1 to 70% isobutane can be mixed with the azeotrope to produce compositions with vapor pressures that stay within the range of about 50 to 60 psig. Similar considerations apply to FIG. 2. It will be observed that the concentration of butane can be varied between 1 and 39% while the vapor pressure remains in the relatively narrow range of about 50 to 60 psig.

While the preferred mixture of FC-22, dimethyl ether and isobutane or butane are those in which the ratio of FC-22 to dimethyl ether corresponds to the azeotrope of these two components (i.e., a 40:60 ratio of FC-22 to DME), it can be seen from the triangular coordinate charts that vapor pressures within the range of about 50 to 60 psig can also be obtained in three-component mixtures where the ratio of FC-22 to DME falls on either side of the azeotrope. For example, 1–70% isobutane can be added to a 50/50 mixture of FC-22 DME and to a 30/70 mixture of FC-22 and DME without substantially modifying the vapor pressure of the propellant. Thus, the broad embodiment of this invention comprises three-component compositions of FC-22, dimethyl ether and butane ot isobutane or mixtures thereof in which the vapor pressure is in the range of about 50 to 60 psig. This would include compositions in which the ratio of FC-22 and DME components are in the ratio of 40:60 and those in which the FC-22/DME is outside this ratio but within the specified vapor pressure range. The proportion of components in such compositions containing isobutane can be readily ascertained from FIG. 1 while those containing butane can be found in FIG. 2.

The tendency for little variation in vapor pressure over a wide range of compositions is considered to be unexpected. The present invention involves, the essence, the incorporation of additional components (i.e., butane of isobutane) with the EC-22/dimethyl ether azeotrope. Since an azeotrope behaves in liquid/vapor equilibrium as if it were a single compound, it might be expected that with the addition of appreciable quantities of a third component, the vapor pressure of the admixture would be somewhere in the middle area between that of the azeotrope and the third component. However, within the defined limits of the present invention there is essentially little change from the vapor pressure of the azeotrope itself.

The vapor pressures of the propellant gas systems of the present invention fall within a desirable vapor pressure range for aerosol propellants, and there is substantially little change in such pressures as the amount of butane or isobutane is varied within the limits set forth herein. Further, the presence of FC-22 and DME contribute lower flammability characteristics to the composition as compared to hydrocarbon propellant blend of similar vapor pressure; i.e., FC-22 is non-flammable and DME is less flammable than butane or isobutane. Although the gas mixture of the present invention is itself flammable and explosion-proof equipment should be used in the loading of aerosol cans, the presence of fluorocarbon 22 in the mixture will reduce the flammability of many aerosol products to such a degree that special labeling is not required under the Federal Hazardous Substances Act. Even though flammable, butane or isobutane are important in the ternary composition, for they impart cost effectiveness as a result of their lower price versus FC-22 or DME. Thus, the present invention offers the producers of aerosol products the opportunity to adjust flammability and cost in an aerosol propellant blend without significant change in pressure.

EXAMPLES

The following examples are typical of the aerosol propellant systems of the present invention and their use in aerosol products. These examples are presented for purposes of illustration only, and are not intended as a limitation on the scope of the invention as described herein.

Procedure

Examples 1–5 were prepared using the following procedure. The active ingredients were weighed into a six-ounce three-piece aerosol can 2⅛" in diameter and 4⅞" long. The can was purged with dichlorodifluoromethane (FC-12) vapor to displace the air in the container. The aerosol can valve was then placed into the can and crimped. The propellants were introduced into the can as liquids through the aerosol valve. Volume amounts corresponding to the weights of the propellants were calculated prior to loading, and a glass, calibrated, pressure buret was used to measure and transfer the liquids from storage cylinders to the can. A nitrogen gas pressure of 100 psig was applied to the buret to aid in transferring the liquids from the buret to the can. After the propellant was loaded, the can was weighed, and the weight of propellant recorded. The loaded can was placed in a 70° F. water bath for 30 minutes and the pressure was then measured with a pressure gauge. Also included in each example is the vapor pressure for the propellant mixture without active ingredients. These values were obtained from the triangular charts in the drawings. The flame extension and flashback tests were conducted by spraying the samples across a candle flame from a distance of six inches and recording how far the flame extended beyond the candle and how far it is flashed back towards the can. The preparation and testing of the sample of Example 6 also used the procedures described above, except that the aerosol ingredients were loaded into a clear, plastic-coated, four-ounce, glass aerosol bottle instead of an aerosol can.

EXAMPLE 1

An illustrative of a system useful as an air freshener is as follows:

| Formulation | Wt. % of Propellant | Wt. % of Total Ingredients | Grams/Can |
|---|---|---|---|
| Active Ingredients | — | 0.50 | 0.50 |
| Fragrance Oil | | | |
| Propellant | | | |
| FC-22 | 19.9 | 19.8 | 19.9 |
| DME | 29.8 | 29.7 | 29.8 |
| Isobutane | 50.3 | 50.0 | 50.2 |
| Vapor pressure of Propellant (psig at 70° F.) | | 55 | |
| Vapor Pressure of filled can (psig at 70° F.) | | 57 | |
| Flame Extension (inches) | | 8–10 intermittent | |
| Flashback (inches) | | 0 | |
| Valve | | Precision Valve | |
| body (inches) | | .080 | |
| stem (inches) | | .018 | |
| actuator (inches) | | .018 | |

This aerosol formulation exhibits a very fine spray and is less flammable than an aerosol formulation propelled with hydrocarbon propellants alone. It is more cost-effective than a room freshener propelled with the FC-22/DME azeotrope alone, and yet has a vapor pressure almost identical to the azeotrope (55 psig at 70° F.).

EXAMPLE 2

An illustration of a system useful as a dry-type antiperspirant is as follows:

| Formulation | Wt. % of Propellant | Wt. % of Total Ingredients | Grams/Can |
|---|---|---|---|
| Active Ingredients | | | |
| Aluminum chlorhydrate | — | 3.5 | 3.5 |

| Formulation | Wt. % of Propellant | Wt. % of Total Ingredients | Grams/Can |
|---|---|---|---|
| Fuming silica | — | 0.2 | 0.2 |
| Hydrated Aluminum silicate/isopropyl myristate | — | 6.0 | 6.0 |
| Perfume | — | 0.3 | 0.3 |
| Propellant | | | |
| FC-22 | 24.9 | 22.4 | 22.5 |
| DME | 37.3 | 33.6 | 33.8 |
| n-Butane | 37.8 | 34.0 | 34.1 |
| Vapor Pressure of Propellant (psig at 70° F.) | 51 | | |
| Vapor Pressure of filled can (psig at 70° F.) | 52 | | |
| Flame Extension (inches) | 9 | | |
| Flashback (inches) | 0 | | |
| Valve | Seaquist NS-44 | | |
| body | Capillary | | |
| stem (inches) | 2 × .020 | | |
| vapor tap (inches) | .020 | | |
| actuator (inches) | Excel 100 Powdermate .020 | | |

This formulation is expelled as a fine dry spray which effectively transmits the active ingredients.

EXAMPLE 3

An illustration of a system useful as an industrial and automotive lubricant is as follows:

| Formulation | Wt. % of Propellant | Wt. % of Total Ingredients | Grams/Can |
|---|---|---|---|
| Active Ingredients Mineral Oil | — | 5.0 | 5.0 |
| Propellant | | | |
| FC-22 | 32.1 | 30.5 | 30.6 |
| DME | 48.2 | 45.8 | 45.9 |
| n-Butane | 19.7 | 18.7 | 18.7 |
| Vapor Pressure of Propellant (psig at 70° F.) | | 54 | |
| Vapor Pressure of filled can (psig at 70° F.) | | 60 | |
| Flame Extension (inches) | | 10 intermittent | |
| Flashback (inches) | | 0 | |
| Valve | | Precision Valve | |
| body (inches) | | .080 | |
| stem (inches) | | .018 | |
| actuator (inches) | | .018 | |

EXAMPLE 4

An illustration of an effective space insecticide is as follows:

| Formulation | Wt. % of Propellant | Wt. % of Total Ingredients | Grams/Can |
|---|---|---|---|
| Active Ingredients | | | |
| Natural pyrethrins | — | 1.5 | 1.5 |
| Piperonyl butoxide | — | 0.5 | 0.5 |
| Polyglycerol fatty acid ester surfactant | — | 1.0 | 1.0 |
| Ethyl alcohol (cosmetic grade) | — | 10.1 | 10.0 |
| Water | — | 52.2 | 52.0 |
| Propellant | | | |
| FC-22 | 17.1 | 5.9 | 5.9 |
| DME | 25.7 | 8.9 | 8.9 |
| Isobutane | 57.2 | 19.9 | 19.8 |
| Vapor Pressure of Propellant (psig at 70° F.) | | 53 | |

-continued

| Formulation | Wt. % of Propellant | Wt. % of Total Ingredients | Grams/Can |
|---|---|---|---|
| Vapor Pressure of filled can (psig at 70° F.) | | 54 | |
| Flame Extension (inches) | | 0 | |
| Flashback (inches) | | 0 | |
| Valve | | Precision Valve | |
| stem (inches) | | 2 × .020 | |
| body (inches) | | .062 | |
| vapor tap (inches) | | .018 | |
| actuator (inches) | | .018 | |

EXAMPLE 5

An illustration of a system useful as a foam shave cream is as follows:

| Formulation | Wt. % of Propellant | Wt. % of Total Ingredients | Grams/Can |
|---|---|---|---|
| Active Ingredients | | | |
| Cetyl Alcohol | — | 4.0 | 4.0 |
| Sorbic Acid | — | 0.2 | 0.2 |
| Polyoxyethylene 21 stearyl ether surfactant | — | 2.0 | 2.0 |
| Water | — | 89.6 | 89.8 |
| Propellant | | | |
| FC-22 | 25.7 | 1.1 | 1.1 |
| DME | 38.6 | 1.6 | 1.6 |
| n-Butane | 35.7 | 1.5 | 1.4 |
| Vapor Pressure of Propellant (psig at 70° F.) | 51 | | |
| Vapor Pressure of filled can (psig at 70° F.) | 44 | | |
| Valve | Precision Valve | | |
| body (inches) | .080 | | |
| stem (inches) | .018 | | |
| actuator | 02–19 series foam spout | | |

EXAMPLE 6

An illustration of a system useful as a cologne is as follows:

| Formulation | Wt. % of Propellant | Wt. % of Total Ingredients | Grams/Bottle |
|---|---|---|---|
| Active Ingredients | | | |
| Fragrance Oil | — | 5.0 | 4.0 |
| Ethyl Alcohol (cosmetic grade) | — | 69.4 | 56.0 |
| Propellant | | | |
| FC-22 | 23.7 | 6.1 | 4.9 |
| DME | 35.3 | 9.0 | 7.3 |
| Isobutane | 41.0 | 10.5 | 8.5 |
| Vapor pressure of Propellant (psig at 70° F.) | 57 | | |
| Vapor Pressure of filled bottle (psig at 70° F.) | 24 | | |
| Flame Extension (inches) | 10 | | |
| Flashback (inches) | 5 | | |
| Valve | Emson bottle valve, S20T | | |
| stem (inches) | .013 | | |
| gasket | S-8501 | | |
| actuator | A-7MB .017 conical | | |

Even though the pressure of the final product is lower than the propellant due to the vapor pressure lowering influence of ethanol, it is much higher than expected.

Calculation of the theoretical pressure from Raoult's Law gives a value of only 2 psig which is insufficient for aerosol use.

We claim:

1. An aerosol propellant composition consisting essentially of monochlorodifluoromethane and dimethyl ether where the monochlorodifluoromethane to dimethylether weight ratio is from 50:50 to 30:70, in admixture with a hydrocarbon selected from the group consisting of butane and isobutane and mixtures thereof said composition having a vapor pressure in the range of about 50–60 psig at 70° F.

2. The composition of claim 1 in which the hydrocarbon is insobutane and the components of the composition are as set forth in FIG. 1 for compositions having a vapor pressure of 50–60 psig at 70° F.

3. The composition of claim 1 in which the hydrocarbon is butane as the components of the composition are as set forth in FIG. 2 for compositions having a vapor pressure of 50–60 psig at 70° F.

4. An aerosol propellant composition consisting essentially of an azeotrope of monochlorodifluoromethane and dimethyl ether in a 40/60 weight ratio in admixture with a hydrocarbon selected from the group consisting of butane and isobutane and mixtures thereof, the proportion of the azeotrope to hydrocarbon being such that the vapor pressure of the mixture is in the range of about 50–60 psig at 70° F.

5. The composition of claim 4 in which the hydrocarbon is butane.

6. The composition of claim 5 in which butane constitutes 1–39% by weight of the propellant composition.

7. The composition of claim 4 in which the hydrocarbon is isobutane.

8. The composition of claim 7 in which the isobutane is present in an amount of about 1–70% by weight.

9. The composition of claim 7 in which the isobutane is present in an amount of about 50–70% by weight.

* * * * *